United States Patent [19]

Inoue et al.

[11] Patent Number: 5,608,123
[45] Date of Patent: Mar. 4, 1997

[54] PROCESS FOR CATALYTIC HYDRATION OF OLEFINS

[75] Inventors: Kaoru Inoue; Masao Iwasaki; Naohiro Ueda, all of Yokohama, Japan

[73] Assignee: Mitsui Toatsu Chemicals, Inc., Tokyo, Japan

[21] Appl. No.: 496,189

[22] Filed: Jun. 28, 1995

[30] Foreign Application Priority Data

Jul. 5, 1994 [JP] Japan .................................. 6-153776
Nov. 29, 1994 [JP] Japan .................................. 6-295086

[51] Int. Cl.$^6$ .................................................. C07C 29/04
[52] U.S. Cl. ..................... 568/899; 502/158; 502/168; 502/402; 502/407; 568/895
[58] Field of Search ........................... 568/895, 899; 502/11, 158, 168, 402, 407

[56] References Cited

U.S. PATENT DOCUMENTS

| | | |
|---|---|---|
| 4,306,101 | 12/1981 | Slaugh et al. . |
| 4,340,769 | 7/1982 | Brandes et al. . |
| 4,886,918 | 12/1989 | Sorensen et al. . |
| 5,012,014 | 4/1991 | Child et al. . |
| 5,371,154 | 12/1994 | Brandvold et al. ................... 525/424 |

FOREIGN PATENT DOCUMENTS

| | | |
|---|---|---|
| 43-8104 | 3/1968 | Japan . |
| 49-117412 | 11/1974 | Japan . |
| 58-7614 | 2/1983 | Japan . |
| 2253851 | 1/1990 | Japan . |
| 6025420 | 2/1994 | Japan . |
| 1381455 | 1/1975 | United Kingdom . |

OTHER PUBLICATIONS

"Catalytic Synthesis of 2–Propanol from a Propylene–Oxygen–Water Mixture Over Pd–Cu Zeolite", Vol. 111, pp. 457–459 (1988).

*Primary Examiner*—Melvyn I. Marquis
*Assistant Examiner*—D. Aylward
*Attorney, Agent, or Firm*—Burns, Doane, Swecker & Mathis

[57] ABSTRACT

There is provided a process for reacting water and olefin such as ethylene or propylene under mild conditions in the presence of a polyorganosiloxane contaminating sulfonic acid groups to produce alcohol corresponding to the olefin with high yield and selectivity.

18 Claims, No Drawings

PROCESS FOR CATALYTIC HYDRATION OF OLEFINS

BACKGROUND OF THE PRESENT INVENTION

1. Field of the Invention

The present invention relates to a novel process for producing alcohols through the hydration of olefins. More particularly, the present invention relates to a process for producing alcohols through the direct hydration of olefins characterized by the use of heterogeneous solid catalysts.

2. Description of the Related Art

Vapor and liquid phase reactions have been carried out industrially for the production of alcohols by the direct hydration of olefins.

An examples of the vapor phase reaction is disclosed in Japanese Patent Laid-open No. 3-207728 in which macroporous cation-exchange resin is used as a catalyst. Another example of the vapor phase reaction is disclosed in Japanese Patent Laid-open No. 55-124541 in which a montmorillonite-containing clay is used as a catalyst. More widely industrialized processes use catalysts carrying phosphoric acid on catalyst supports, as disclosed in Japanese Patent Laid-open Nos. 53-84906 and 52-133095 and Japanese Patent Publication No. 51-44915.

In these processes for producing alcohols by using the vapor phase reactions the reaction is generally conducted in a high temperature range to provide less conversion of olefins. These processes thus produce small amounts of alcohol per unit volume of a reactor and require a large amount of non-reacted olefins to be recycled, which is not advantageous considering the facility and energy required. In addition, these common industrial processes using a supported phosphoric acid catalyst are disadvantageous in that the phosphoric acid used as the catalyst component volatilizes during reactions to cause deterioration of the catalytic capabilities.

In this respect, the so-called liquid phase reaction is well-known, which comprises contacting olefins with water in a liquid state, as a solution for the problems inherent to the vapor phase reaction, such as low productivity of alcohols and the necessity for recycling a large amount of non-reacted olefins. For example, Japanese Patent Publication Nos. 43-8104 and 43-16123 disclose a process using an aromatic sulfonic acid as a homogeneous catalyst while Japanese Patent Publication Nos. 49-166, 50-35051 and 49-36204 and Japanese Patent Laid-open No. 53-9746 disclose heteropolyacids as a catalyst.

However, these homogeneous catalysts can be separated and recovered from the mixture of the catalyst and products (especially water, one of the raw materials) through troublesome procedures with much energy required for the treatment. Furthermore, these acid catalysts are uniformly dissolved in the liquid phase and the liquid is thus in contact with a device such as a reactor, with the possibility of corrosion of the inner walls of the reactor. The use of expensive materials for the device is therefore inevitable and hence it is not economical.

To overcome the defects of the homogeneous catalyst mentioned above, heterogeneous solid catalysts have been used in the liquid phase reaction. For example, the use of strong acidic cation exchange resins as catalysts is disclosed in Japanese Patent Publication Nos. 44-26656, 58-7614, and 63-27332 and Japanese Patent Laid-open Nos. 49-117412 and 61-230744. The use of zeolite catalysts is disclosed in International Publication Nos. 3-502321 and 3-503175, Japanese Patent Laid-open Nos. 1-246234, 1-246233 and 63-218251. Strong acidic cation exchange resins have higher activities under the reaction conditions of lower temperature and pressure (about 150° C. and about 100 atm.) in comparison with the homogeneous liquid catalyst mentioned above. However, cation exchange resins themselves have a heat resistance temperature of about 100° C., and hence using them at a temperature of 150° C. means that reactions are performed under constant deterioration of the catalyst and that acidic components such as sulfonic acid are decomposed and eliminated to effuse inevitably into the reaction solutions. The catalytic activities, therefore, are reduced and the effused acidic components have a possibility of corroding the equipment. Accordingly, the use of expensive materials of corrosion resistance is inevitable for the equipment, which is economically disadvantageous. In addition, the cation exchange resins mentioned above are weak in mechanical strength and have a disadvantage of being destroyed during the process.

In comparison with these catalysts, heterogeneous zeolite catalysts are insufficient in their activities and are not expected to have strong catalytic activities comparable to strong acidic cation exchange resins. Moreover, they require high reaction temperature to obtain sufficient yields of alcohols.

Nevertheless, it apparently enhances decomposition of the zeolite compounds and the elimination of aluminum to heat zeolite compounds to a high temperature required for the hydration of olefins in the presence of water in the liquid state. Therefore, the production of alcohols at a desired reaction rate is practically impossible.

SUMMARY OF THE INVENTION

In order to overcome the disadvantages of conventional heterogeneous liquid phase catalysts, the present inventors carried out research focusing considerable attention on the high productivity of liquid phase reactions and advantages of conventional heterogeneous solid catalysts in liquid phase reactions for the production of alcohols by direct catalytic hydration reactions of olefins with water. The research findings were that polyorganosiloxanes containing sulfonic acid groups are heat resistant, solid catalysts with high catalytic activities. Particularly, these polyorganosiloxanes become highly stable and active by coating and/or silylation treatment with silica, polyorganosiloxanes, sililating agents containing hydrocarbon groups. The present invention was thus completed.

By using heterogeneous solid catalysts of the present invention, catalytic hydration reactions in the liquid phase do not cause decomposition such as thermal decomposition of the catalysts to effuse the acidic portion into the liquid phase even at a high temperature, the catalyst hold their activities for a long period. The disadvantage of corroding equipment by acid is overcome, which allows the effective production of alcohols.

Therefore, it is an object of the present invention to provide a process for high efficient production of alcohols by direct hydration of olefins in the liquid phase so that a catalyst and reaction solution can be readily separated and equipment do not suffer corrosion.

Another object of the present invention is to provide a catalyst which holds its activity over a wide range of temperature during the hydration reaction in the vapor or liquid phase.

In accordance with the present invention, the following results were obtained:

1. Alcohols can be produced in high yields and selectivity by direct hydration of olefins.

2. In comparison with conventional processes, alcohols can be produced by direct hydration under mild conditions of lower temperature and pressure as well as under the conditions that corrosion of equipment hardly occurs.

3. Alcohols which are of industrial importance can be produced advantageously in regard to safety, process and economy.

4. Alcohols can be produced without thermal decomposition of catalysts and without neutralization treatment of reaction solutions.

5. Stable heterogenous solid catalysts can be provided for the production of alcohols.

DETAILED DESCRIPTION OF THE INVENTION

The present invention provides a production process of alcohols by the reaction of olefins with water in the presence of polyorganosiloxane containing sulfonic acid groups.

The present invention is described in more detail below.

Olefins used in the present invention are aliphatic hydrocarbons which possess at least one carbon-carbon double bond; i.e. straight or branched monoolefins and polyolefins. Also, these olefins may contain a halogen atom, a hydroxyl group, a nitro group, an amino group, a cyano group, a carbonyl group, an acetoxy group, an aromatic group, a carboxyl group, a mercapto group, etc. as a substituent. Preferably these olefins should be aliphatic olefins having carbon atoms of from 2 to 6.

Examples of these olefins include ethylene, propylene, 1-butene, 2-butene, isobutene, straight or branched pentenes such as 1-pentene, 2-pentene, 2-methyl-1-butene and 2-methyl-2-butene, straight or branched hexenes such as 1-hexene, 2-hexene, 3-hexene and methyl pentenes and polyolefins such as butadiene, pentadiene and hexadiene. In addition, alicyclic olefins such as cyclopentene, methylcyclopentene, cyclohexene, methylcyclohexene, cyclooctene, methylcyclooctenes, cyclopentadienes, cyclohexadienes and cyclooctadienes may be used. More preferably the olefins involve at least one selected from the group consisting of lower olefins having carbon atoms of from 2 to 6 such as ethylene, propylene, n-butenes, i-butene and cyclohexene.

The present invention uses one or more species of these olefins for reaction.

Furthermore, the purity of olefins used in the present invention is not particularly limited so that olefins of general reagent grade, of industrial grade, and diluted with alkanes, etc. can be used.

According to the present invention, alcohols corresponding to olefins are produced by contacting the olefins mentioned above with water in the presence of a polyorganosiloxane catalyst having sulfonic acid groups to cause addition of water to the olefins.

Polyorganosiloxanes having sulfonic acid groups used as a catalyst in the present invention, have a structure that hydrocarbon groups partially possessing sulfonic acid groups are directly bonded through carbon-silicon bonds to silicon atoms in the siloxane matrix consisting of siloxane bonds.

These siloxanes have the mean carbon-silicon bond count per a silicon atom in the siloxanes of 0.05 to 3, preferably 0.1 to 2 and more preferably 0.2 to 1.

These hydrocarbon groups are preferably substituted or unsubstituted alkyl groups having sulfonic acid groups or substituted or unsubstituted aromatic hydrocarbon groups having sulfonic acid groups. In particular, if the hydrocarbon groups having sulfonic acid groups contain aromatic groups, the carbon-silicon bonds may be the bonds directly linking carbons in the aromatic hydrocarbon groups to silicons or the bonds linking carbons in the hydrocarbon groups having aromatic groups as substituents to silicons.

Also, all of these hydrocarbon groups may contain one or more sulfonic acid groups and some of these hydrocarbons groups may contain sulfonic acid groups. Possession of sulfonic acid groups in all the hydrocarbon groups is preferable. However, catalysts in the present invention are not limited by the amount of sulfonic acid groups therein.

Catalysts used in the present invention, as described above, are polyorganosiloxanes having sulfonic acid groups and additionally become more preferable polyorganosiloxane catalysts having sulfonic acid groups by silica coating, polyorganosiloxane coating and/or silylation treatment with an alkoxysilane, a halogenated silane, a substituted alkoxysilane with alkyl groups and/or aromatic groups and a substituted halogenated silane with alkyl groups and/or aromatic groups.

The present invention uses as catalysts these polyorganosiloxanes having sulfonic acid groups.

In the present invention, preparation processes of these catalysts are not limited, and any process that produces hydrocarbon groups having sulfonic acid groups containing direct carbon-silicon bonds in the siloxane matrix are allowed. The following preparation processes, for example, can be used as easily available processes to be carried out. However, the present invention is not limited to only these preparation processes.

Easily available preparation processes to be carried out, for example, include the one in which silane compounds represented by the general formula: $(R_a)nSi(X)_{4-n}$ (wherein $R_a$ is a hydrocarbon group having at least one sulfonic acid group; $(R_a)_n$ may be same or different; Si is a silicon atom, X is at least one selected from the group consisting of an alkoxyl group and a halogen atom and n is an integer of 1 to 3, preferably 1 to 2.) are hydrolyzed and the one in which a mixture of the silane compounds described above and silane compounds represented by the general formula $Si(X)_4$ (wherein Si is a silicon atom and X is at least one selected from the group consisting of an alkoxyl group and a halogen atom) is hydrolyzed.

In these processes, the hydrolysis mentioned above may be carried out after the protons of sulfonic acid groups in $R_a$ are replaced by metal cations to form sulfonates and then the polyorganosiloxanes obtained may be treated by acids to form sulfonic acid groups.

Moreover the materials fixed silane compounds represented by the above general formula, $(R_a)_nSi(X)_{4-n}$, by silylation on silica gel are effective catalysts in the present invention.

Also, another easily available preparation process to be carried out is hydrolyzing silanes represented by the formula: $(R_b)_nSi(X)_{4-n}$ (wherein $R_b$ is a hydrocarbon group into which sulfonic acid groups can be introduced by sulfonation and may be same or different, Si is a silicon atom, X is at least one selected from the group consisting of an alkoxyl group and a halogen atom and n is an integer of from 1 to 3, preferably from 1 to 2) or hydrolyzing a mixture of these silanes and silane compounds represented by the formula: $Si(X)_4$ (wherein Si is a silicon atom and X is at least one selected from the group consisting of an alkoxyl group and a halogen atom), and then sulfonating the hydrolysis products obtained to produce polyorganosiloxanes having sulfonic acid groups. Moreover, equally effective catalysts in the present invention include compounds sulfonated after fixing silane compounds represented by the above formula: $(R_b)_n Si(X)_{4-n}$ onto silica gel by silylation.

The hydrocarbon groups $R_a$ and $R_b$ represented in the above formulae are described as follows.

Any hydrocarbon group can be used as $R_a$ in the present invention if the group is a hydrocarbon group having at least one sulfonic acid group ($-SO_3H$). However, the hydrocarbon group is at least one selected from the group consisting of a substituted or unsubstituted aromatic hydrocarbon group having at least one sulfonic acid group, preferably having from 6 to 20 carbon atoms, more preferably having from 6 to 15 carbon atoms (the sulfonic acid group may be substituted directly on the aromatic group or on the hydrocarbon group on which the aromatic group is substituted) and a substituted or unsubstituted aliphatic and/or alicyclic saturated hydrocarbon group having at least one sulfonic acid group, preferably having from 1 to 15 carbon atoms, more preferably having from 1 to 10 carbon atoms.

Examples of the hydrocarbon groups mentioned above include aromatic groups such as a phenyl group, a tolyl group, a xylyl group, a naphthyl group and a methylnaphthyl group, in which at least one sulfonic acid group is substituted on the aromatic ring, and aromatic group substituted-alkyl groups such as a benzyl group and a naphtylmethyl group, in which at least one sulfonic acid group is substituted on the aromatic ring, and a methyl group, an ethyl group, a n-propyl group, an i-propyl group, a n-butyl group, an i-butyl group, a t-butyl group, a straight or branched pentyl group, a straight or branched hexyl group, a straight or branched heptyl group, a straight or branched octyl group, a cyclohexyl group, a methylcyclohexyl group and an ethylcyclohexyl group, on each of which at least one sulfonic acid group is substituted. In addition, a halogen atom, an alkoxyl group, a nitro group, an amino group, a hydroxyl group, etc. may be substituted as well as a sulfonic acid group on these aromatic and saturated aliphatic or alicyclic hydrocarbon groups.

Also, any hydrocarbon group can be used as $R_b$ if sulfonic acid groups can be introduced into the hydrocarbon group by various sulfonation processes. Examples of the preferred hydrocarbons include a hydrocarbon group having an aromatic group, a hydrocarbon group having at least one mercapto group ($-SH$), an alkyl group having at least one halogen atom, an olefinic hydrocarbon group having at least one carbon-carbon double bond and a hydrocarbon group having at least one epoxy group. However, the present invention is not limited to these hydrocarbon groups.

Any hydrocarbon group having an aromatic group may be used as the above mentioned hydrocarbon group ($R_b$) having an aromatic group. The preferred hydrocarbon group having an aromatic group is, however, an aromatic group or a hydrocarbon group on which at least one aromatic group is substituted (e.g., an alkyl group on which an aromatic group is substituted) both of which have from 6 to 20 carbon atoms, more preferably have from 6 to 15 carbon atoms. Examples of these hydrocarbons include aromatic groups such as a phenyl group, a tolyl group, a xylyl group, a naphthyl group and a methylnaphthyl group, and alkyl groups on which aromatic groups are substituted such as a benzyl group and a naphtylmethyl group.

Also, those hydrocarbon groups may be hydrocarbons having substituent groups such as a halogen atoms, an alkoxyl group, a nitro group, an amino group and a hydroxyl group.

Any hydrocarbon group having at least one mercapto group may be used, but mono or polymercapto-substituted alkyl groups preferably having from 1 to 15 carbon atoms, more preferably having from 1 to 10 carbon atoms, or mono or polymercapto-substituted aromatic hydrocarbons preferably having from 6 to 20 carbon atoms, more preferably having from 6 to 15 carbon atoms are desirable. Examples of these hydrocarbons include a mercaptomethyl group, a 2-mercaptoethyl group, a 3-mercapto-n-propyl group, a 4-mercapto-n-butyl group, a 4-mercaptocyclohexly group, p-mercaptophenyl group, a p-mercaptomethylphenyl group, a p-mercaptobenzyl group and a 4-mercaptonaphthyl group. In addition, a halogen atom, an alkoxyl group, a nitro group, an amino group, a hydroxyl group, etc. may be substituted for these hydrocarbon groups as well as a mercapto group.

Moreover, any alkyl group having at least one halogen atom may be used. The number of halogen atoms is not limited and any alkyl group wherein halogen atoms are substituted for at least one hydrogen atom bonded to the alkyl group may be used. In particular halogenated alkyl groups having from 1 to 15 carbon atoms are preferable and halogenated alkyl groups having from 1 to 10 carbon atoms are more preferable. It is recommended that the alkyl groups contain at least one selected from the group consisting of a chlorine atom, a bromine atom and a iodine atom. More specific examples of these halogenated groups include a chloromethyl group, a bromomethyl group, a dichloromethyl group, a iodomethyl group, a diiodomethyl group, a 2-chloroethyl group, a 1,2-dichloroethyl group, a 2-bromoethyl group, a 2-iodoethyl group, a 3-chloro-n-propyl group, a 3-bromo-n-propyl group, a 4-chloro-n-butyl group, a 4-bromo-n-butyl group, a 4-chlorocyclohexyl group and a 4-bromocyclohexly group. In addition, these groups may be hydrocarbon groups having a substituent group such as an alkoxyl group, a nitro group, an amino group and a hydroxyl group as well as a halogen atom.

Any olefinic hydrocarbon group containing at least one carbon-carbon double bond may be used. Aromatic hydrocarbon groups having as substituent groups olefinic hydrocarbons and preferably having from 8 to 20 carbon atoms, more preferably having from 8 to 15 carbon atoms and aliphatic or alicyclic olefinic hydrocarbon groups preferably having from 2 to 15 carbon atoms, more preferably having from 2 to 10 carbon atoms are desirable. Examples of the aromatic hydrocarbon groups having olefinic hydrocarbons as substituent groups include a 4-vinylphenyl group, a 4-vinylnaphthyl group and a 4-allylphenyl group, and examples of the aliphatic or alicyclic olefinic hydrocarbon groups include a vinyl group, an allyl group, n-butenyl groups, cyclohexenyl groups, methylcyclohexenyl groups and ethylcyclohexenyl groups. These hydrocarbon groups may be olefinic hydrocarbon groups having substituent groups such as an alkoxyl group, a nitro group, an amino group and a hydroxyl group.

Any hydrocarbon group having at least one epoxy group (an oxirane group) may be used. Aromatic hydrocarbon groups having epoxy groups as substituent groups and preferably having from 8 to 20 carbon atoms, more preferably having from 8 to 15 carbon atoms and aliphatic or alicyclic hydrocarbon groups having epoxy groups as substituent groups and preferably having from 2 to 15 carbon atoms, more preferably having from 2 to 10 carbon atoms are desirable. Examples of the aromatic hydrocarbon groups having epoxy groups as substituent groups include a p-epoxyethylphenyl group, a 4-epoxyethylnaphthyl group, a p-(2,3-epoxypropyl)phenyl group, a p-(3,4-epoxycyclohexyl)phenyl group, etc. and examples of the aliphatic or alicyclic hydrocarbon groups having epoxy bonds include an epoxyethyl group, a 2,3-epoxypropyl group, a 3-glycidoxypropyl group, a 3,4-epoxycyclohexyl group, 2-(3,4-epoxycyclohexyl)ethyl group, etc. These hydrocarbon groups may also contain an alkoxyl group, a nitro group, an amino group, a hydroxyl group, etc.

These hydrocarbons are, of course, enumerated only to help illustrate the present invention, and the present invention is not limited thereto.

Upon preparing a catalyst by use of a silane compound represented by the formula: $(R_b)_n Si(X)_{4-n}$, this silane compound by itself or a mixture of this silane compound and a silane compound represented by the formula: $SiX_4$ is hydrolyzed, or a silane compound represented by the formula: $(R_b)_n Si(X)_{4-n}$ is silylized and fixed on silica gel, and then sulfonated to form polyorganosiloxanes having sulfonic acid groups.

Sulfonation reactions in the present invention are unlimited particularly as to their recipes and any recipe by which hydrocarbon groups represented by $R_b$ are converted into hydrocarbon groups having sulfonic acid groups may be used. It is also natural that their recipes are varied according to $R_b$ species.

Easily available processes to be carried out for sulfonation are illustrated hereafter. If the polyorganosiloxanes are obtained from a silane compound of which $R_b$ is a hydrocarbon group containing aromatic groups, polyorganosiloxanes having sulfonic acid groups can be produced by ordinary sulfonation to aromatic compounds in which the polyorganosiloxanes are contacted with sulfuric acid or chlorosulfonic acid.

Also, if the polyorganosiloxanes are obtained from a silane compound of which $R_b$ is a hydrocarbon group containing at least one mercapto group, polyorganosiloxanes having sulfonic acid groups can be produced by oxidizing them with various oxidizing agents (e.g., nitric acid and hydrogen peroxide) or by an addition reaction (addition of SH to olefins) of them to olefin compounds containing sulfonic acid groups.

In the treatment above, olefin compounds containing sulfonic acid groups, which are used for sulfonation, are olefinic hydrocarbons containing at least one sulfonic acid group and carbon-carbon double bond. Examples of these olefin compounds include vinyl sulfonic acid, allyl sulfonic acid, methallyl sulfonic acid, styrene sulfonic acid, cyclohexene sulfonic acid, etc.

Moreover, if the polyorganosiloxanes are obtained from a silane compound of which $R_b$ is an alkyl group containing at least one halogen atom, polyorganosiloxanes having sulfonic acid groups can be produced by heating and contacting them with a solution of a metal sulfite (e.g., sodium sulfite and potassium sulfite). If the polyorganosiloxanes are obtained from a silane compound of which $R_b$ is an olefinic hydrocarbon group containing at least one carbon-carbon double bond, polyorganosiloxanes having sulfonic acid groups can be produced by contacting them with a solution of a metal hydrogen sulfite (e.g., sodium hydrogen sulfite and potassium hydrogen sulfite) in the presence of an oxidizing agent (e.g., oxygen). Moreover, if the polyorganosiloxanes are obtained from a silane compound of which $R_b$ is a hydrocarbon group containing at least one epoxy bond (oxirane), polyorganosiloxanes having sulfonic acid groups can be produced by contacting them with a solution of a metal hydrogen sulfite (e.g., sodium hydrogen sulfite and potassium hydrogen sulfite).

Upon sulfonation using a metal hydrogen sulfite, sulfonation in the presence of a metal sulfite as well as the metal hydrogen sulfite is recommended here. However, the processes used in the present invention are, of course, not limited thereto.

The processes described in the present invention use polyorganosiloxanes having sulfonic acid groups as catalysts. In addition, if the polyorganosiloxanes having sulfonic acid groups are coated and/or silylated with at least one of silane compounds represented by the general formula: $(R)_n Si(X)_{4-n}$ (wherein R represents at least one hydrocarbon group selected from the group consisting of aliphatic or alicyclic hydrocarbon groups having from 1 to 10 carbon atoms and aromatic hydrocarbon groups having from 6 to 15 carbon atoms, X is at least one selected from the group consisting of an alkoxyl group and a halogen atom, n is 0 or an integer of from 1 to 3 and Si is a silicon atom), the catalysts work more effectively. The coating and/or silylation treatment enhances the lifetime of the catalysts and further increases the activities.

The coating and/or silylation treatment in the present invention is described hereafter.

As mentioned above, a polyorganosiloxane catalyst having sulfonic acid groups in the present invention becomes a more preferable catalyst by the coating and/or silylation treatment with a silane compound represented by the aforementioned formula: $(R)_n Si(X)_{4-n}$.

In a silane compound represented by the aforementioned formula: $(R)_n Si(X)_{4-n}$, R is at least one hydrocarbon group selected from the group consisting of aliphatic or alicyclic hydrocarbon groups containing from 1 to 10 carbon atoms and aromatic hydrocarbon groups containing from 6 to 15 carbon atoms, and X is at least one selected from the group consisting of an alkoxyl group and a halogen atom.

Examples of R include a methyl group, an ethyl group, a n-propyl group, a i-propyl group, a straight or branched butyl group, a straight or branched pentyl group, a straight or branched hexyl group, a straight or branched octyl group, a straight or branched nonyl group, a straight or branched decyl group, a cyclohexyl group, a 4-methylcyclohexyl group, a phenyl group, a naphthyl group, a p-tolyl group, a p-ethyl phenyl group, a 4-methylnaphthyl group, etc.

In addition, X represents an alkoxyl group or a halogen atom, and the aforementioned formula includes silane compounds having no hydrocarbon groups in the case of n=0.

The coating treatment in the present invention is mixing a polyorganosiloxane having sulfonic acid groups, a catalyst, with a silane compound represented by the formula: $(R)_n Si(X)_{4-n}$ and hydrolyzing the mixture in suspension to form a polysiloxane, a hydrolysis product of the silane compound represented by the formula: $(R)_n Si(X)_{4-n}$, on the polyorganosiloxane having sulfonic acid groups.

The silylation treatment is to directly react silanol groups contained in a polyorganosiloxane having sulfonic acid groups which is a catalyst prepared by the process described above or the like, with a silane compound represented by the formula: $(R)_n Si(X)_{4-n}$ to form siloxane bond and to fix the silane compound thereby on the catalyst.

As silane compounds used for the coating treatment, the one to be n=0 or 1 in the aforementioned formula: $(R)_n Si(X)_{4-n}$ is preferable and as silane compounds used for the silylation treatment, the one to be n=1 to 3 in the formula $(R)_n Si(X)_{4-n}$ is preferable.

In the present invention, when catalysts are subjected to the coating and silylation treatment one or more times like the silylation after the coating treatment, these become preferable ones.

Upon the coating and silylation treatment, inactive solvents for silane compounds represented by the formula: $(R)_nSi(X)_{4-n}$ and a catalyst of polyorganosiloxane having sulfonic acid groups, e.g., alcohol, hexane, heptane, benzene, toluene, etc. are preferably used. Upon the coating treatment, particularly the use of a solvent compatible with water is preferable.

The rate of the coating and/or silylation treatment in the present invention is not limited. However, the coating rate is preferably from 5 to 200% by weight and more preferably from 10 to 100% by weight relative to the total amount of the raw material, i.e., the polyorganosiloxane having sulfonic acid groups. The silylation rate is preferably from 0.1 to 30% by weight and more preferably from 0.5 to 20% by weight relative to the total amount of the raw material, i.e., the polyorganosiloxane having sulfonic acid groups. The present invention is, of course, not limited to these ranges.

X shown in all of the formulae set forth before represents an alkoxyl group and a halogen atom. Upon preparation by the processes described above, polysiloxane bonds, for example, can be formed by breaking silicon-X bonds by hydrolysis and furthermore, siloxane bonds can be produced by subjecting the compound having X to the silylation treatment to react with silanol group on silica gel.

The preferable alkoxyl group is an aliphatic alkoxyl group having from 1 to 10 carbon atoms and an aromatic alkoxyl group having from 6 to 15 carbon atoms. Examples of the alkoxyl group include alkylalkoxyl groups such as a methoxy group, an ethoxy group, a n-propoxy group, an i-propoxy group, a n-butoxy group, a sec-butoxy group and a t-butoxy group and aromatic alkoxyl groups such as a phenoxy group and a naphthoxy group.

As the halogen atom, a chlorine atom, a bromine atom and an iodine atom can be used, and a chlorine atom is preferable. X is, of course, not limited to only these atoms and any combination of these atoms may also be used.

Upon embodiment of the present invention, the ratio of the raw materials, i.e., olefins and water, are not particularly limited, but it is recommended that the water/olefin mole ratio is preferably within the range of 0.1 to 50 and more preferably within the range of 0.3 to 30. This is because a little amount of water makes it difficult to attain a high conversion of raw material olefins. And when water is used more than necessary, although an excess amount of water gives a high conversion of olefins, a reactor becomes larger and the circulation of a large amount of water is required, which does not provide effective production.

Upon embodiment of the present invention, the amount of a catalyst is not limited, but it is recommended that in performing the reaction, for example, in batchwise, the amount of the catalyst is preferably 0.001–100% by weight and more preferably 0.1–50% by weight relative to raw material water.

The use of a little amount of the catalyst substantially lowers the reaction rate extremely and causes a problem in point of efficiency, while the use of an excess amount of the catalyst reduces the stirring efficiency and may cause a trouble.

In addition, the catalyst can be used in the form of powder commonly used or granules molded by extrusion or press.

The reaction temperature, which is not particularly limited, is preferably in the range of 0°–500° C. and more preferably 30°–300° C. If the reaction temperature is extremely low, the conversion of olefins (reactant) becomes low, in other words the reaction rate is extremely reduced and the productivity of reaction products is also reduced. On the other hand, if the reaction temperature is more than 500° C., an undesirable side reaction proceeds to form a large amount of by-products, which is not preferable to the stabilities of raw material olefins and resulting alcohols and reduces the selectivity of reaction so as to be uneconomical.

The reactions can be carried out under reduced, high or ordinary pressure. From the viewpoint of reaction efficiency (reaction efficiency per unit volume), performing the reaction under extremely low pressure is undesirable. Also, from the economical viewpoint of facilities such as a reaction device, performing the reaction under extremely high pressure is undesirable. The generally preferred range of the reaction pressure is 0.5 to 500 atmospheres and more preferably 1 to 300 atmospheres. However, the present invention is not limited only to these ranges of pressure.

Upon embodiment of the present invention, a solvent or a gas inactive to catalysts and reactants is added into the reaction system and the reaction can be carried out under a diluted condition. Examples of such solvents and gases include saturated aliphatic hydrocarbons such as methane, ethane, propane, butane, hexane and cyclohexane and inactive gasses such as nitrogen, argon and helium.

The reaction can be carried out under the liquid phase, vapor phase or mixed vapor-liquid phase, but from the viewpoint of productivity and reactor scale, it is desirable to carry out the reaction under the condition that at least part of water is in a liquid state. However, the present invention is not limited thereto.

In the present invention, any of an ordinary batchwise reaction, a semi-batchwise reaction in which part of raw materials or catalysts are supplied in continuous manner and a continuous flow reaction can be adopted. In addition, the order and process of addition of each component such as reactant raw materials and catalysts are not particularly limited.

As a catalyst filling process, there have been provided various processes such as fixed bed, fluidized bed, suspended bed and plate fixed bed, and any of these processes may be used in the present invention.

The reaction time (residence time or catalytic contact time in a flow reaction) is not particularly limited, but is ordinarily 0.1 seconds to 30 hours, preferably 0.5 seconds to 15 hours.

After completion of the reaction, the reaction product can be separated and recovered from the above mentioned catalyst, etc. by ordinal separation processes such as filtration, extraction and fractionation.

Alcohols, object products, can be separated and purified from the separated and recovered reaction product mentioned above by ordinal separation and purification processes containing a unit process such as solvent extraction, distillation, alkaline treatment and acid treatment, or a combination of these operations. Non-reacted raw materials can be recovered and reused by recycling them back to the reaction system.

Upon a batchwise reaction, the catalyst recovered by separating the reaction product after completion of the reaction can be reused without further treatment, or part of or all of the catalyst can be regenerated and then reused.

Upon reaction by a fixed bed or a continuous flow fluidized bed process, if the catalyst lowers partially or entirely its activity during the reaction, the reaction can be discontinued to regenerate the catalyst and then resumed by using the regenerated catalyst, or without interrupting the reaction, part of the catalyst can be continuously or intermittently taken out to regenerate it and then recycled back to the reactor. Moreover, the unused fresh catalyst can be continuously or intermittently fed to the reactor. Upon a continuous flow moving bed type reaction or a continuous flow catalytic reaction, the catalyst can be separated and recovered to reuse it as well as upon a batchwise reaction.

The following examples are provided to help further illustrate the present invention. However, the present invention is not limited only to those examples.

Preparation of Catalysts (1) Synthesis of polyorganosiloxanes by hydrolysis of a silane compound (1-1) Preparation of polyorganosiloxane partly having halogenated alkyl groups by hydrolysis of a silane compound (Preparation process 1)

3-chloropropyltrimethoxysilane ((ClPr)Si(OMe)$_3$) and tetraethoxysilane (Si(OEt)$_4$) were mixed at the prescribed mixing ratios shown in Table 1 and then 62.5 ml of ethanol was added. The mixture was poured to a 1 liter three necked flask equipped with a stirrer and a condenser and stirred for an hour at 60° C. Next, a 16.7 ml of 0.01 normal hydrochloric acid solution was added to the mixture solution and stirring was continued for 2 hours at 60° C. (if tetraethoxysilane was not mixed, the hydrochloric acid solution was not added and the following operation was carried out). Then a mixture of 15 ml of hexane and 22.5 ml of ethanol was added while stirring at 60° C. and to the solution, was gradually dropped a solution in which 25.0 ml of 28% aqueous ammonia had been dissolved into 135.0 ml of pure water. After completion of dropping, stirring was continued for 10 hours at the same temperature to finish gelation.

After solvents and water were removed from the gelled mixture obtained under reduced pressure to dry, the dried gel was thoroughly washed with water and then dried again for 6 hours at 120° C. to obtain polyorganosiloxane.

Polyorganosiloxanes obtained by the preparation process 1 mentioned above are shown in Table 1.

TABLE 1

| Polyorganosiloxanes | (ClPr)Si(OMe)$_3$: Si(OEt)$_4$ weight | (mole ratio) |
|---|---|---|
| siloxane 1 | 99.38 g:0.0 g | (1:0) |
| siloxane 2 | 49.68 g:52.08 g | (1:1) |
| siloxane 3 | 29.81 g:72.92 g | (1:2.3) |
| siloxane 4 | 9.94 g:93.75 g | (1:9) |

(1-2) Preparation of polyorganosiloxanes partly having phenyl groups by hydrolysis of a silane compound (Preparation process 2)

Phenyltriethoxysilane ((Ph)Si(OEt)$_3$) and tetraethoxysilane (Si(OEt)$_4$) were mixed at the prescribed mixing ratios shown in Table 2 and then 62.5 ml of ethanol was added. The mixture was poured to a 1 liter three necked flask equipped with a stirrer and a condenser and stirred for an hour at 60° C. Next, a 16.7 ml of 0.01 normal hydrochloric acid solution was added to the mixture solution and stirring was continued for 2 hours at 60° C. (if tetraethoxysilane was not mixed, the hydrochloric acid solution was not added and the following operation was carried out). Then a mixture of 15 ml of hexane and 22.5 ml of ethanol was added while stirring at 60° C. and to the solution, was gradually dropped a solution in which 25.0 ml of 28% aqueous ammonia had been dissolved into 135.0 ml of pure water. After completion of dropping, stirring was continued for 10 hours at the same temperature to finish gelation.

After solvents and water were removed from the gelled mixture obtained under reduced pressure to dry, the dried gel was thoroughly washed with water and then dried again for 6 hours at 120° C. to obtain polyorganosiloxane.

Polyorganosiloxanes obtained by the preparation process 2 mentioned above are shown in Table 2.

TABLE 2

| Polyorganosiloxanes | (Ph)Si(OEt)$_3$: Si(OEt)$_4$ weight | (mole ratio) |
|---|---|---|
| siloxane 5 | 120.19 g:0.0 g | (1:0) |
| siloxane 6 | 60.09 g:52.08 g | (1:1) |
| siloxane 7 | 36.06 g:72.92 g | (1:2.3) |
| siloxane 8 | 12.02 g:93.75 g | (1:9) |

(1-3) Preparation of polyorganosiloxanes partly having vinyl groups by hydrolysis of a silane compound (Preparation process 3)

Vinyltriethoxysilane (CH$_2$=CHSi(OEt)$_3$) and tetraethoxysilane (Si(OEt)$_4$) were mixed at the prescribed mixing ratios shown in Table 3 and then 62.5 ml of ethanol was added. The mixture was poured to a 1 liter three necked flask equipped with a stirrer and a condenser and stirred for an hour at 60° C. Next, a 16.7 ml of 0.01 normal hydrochloric acid solution was added to the mixture solution and stirring was continued for 6 hours at 60° C. Then a mixture of 15 ml of hexane and 22.5 ml of ethanol was added while stirring at 60° C. and to the solution, was gradually dropped a solution in which 25.0 ml of 28% aqueous ammonia had been dissolved into 135.0 ml of pure water. After completion of dropping, stirring was continued for 4 hours at the same temperature to finish gelation.

After solvents and water were removed from the gelled mixture obtained under reduced pressure to dry, the dried gel was thoroughly washed with water and then dried again for 6 hours at 120° C. to obtain polyorganosiloxane.

Polyorganosiloxanes obtained by the preparation process 3 mentioned above are shown in Table 3.

TABLE 3

| Polyorganosiloxanes | CH$_2$=CHSi(OMe)$_3$: Si(OEt)$_4$ by weight | (mole ratio) |
|---|---|---|
| siloxane 9 | 47.58 g:52.08 g | (1:1) |
| siloxane 10 | 28.55 g:72.92 g | (1:2.3) |

(1-4) Preparation of polyorganosiloxanes partly having epoxy groups by hydrolysis of a silane compound (Preparation process 4)

2-(3,4-Epoxycyclohexyl)ethyltrimethoxysilane (C$_6$H$_8$OC$_2$H$_2$Si(OMe)$_3$) and tetraethoxysilane (Si(OEt)$_4$) were mixed at the prescribed mixing ratios shown in Table 4 and then 62.5 ml of ethanol was added. The mixture was poured to a 1 liter three necked flask equipped with a stirrer and a condenser and stirred for an hour at 60° C. Next, 7.5 ml of pure water was added to the solution and stirring was continued for 6 hours at 60° C. Then a mixture of 15 ml of hexane and 22.5 ml of ethanol was added while stirring at 60° C. and to the solution, was gradually dropped 200 ml of pure water into which 7 g of anhydrous sodium sulfite had been dissolved. After completion of dropping, stirring was continued for 4 hours at the same temperature to finish gelation.

After solvents and water were removed from the gelled mixture obtained under reduced pressure to dry, the dried gel was thoroughly washed with water and then dried again for 6 hours at 120° C. to obtain polyorganosiloxane.

Polyorganosiloxanes obtained by the preparation process 4 mentioned above are shown in Table 4.

TABLE 4

| Polyorganosiloxanes | $C_6H_8OC_2H_2Si(OMe)_3$: $Si(OEt)_4$ weight | (mole ratio) |
| --- | --- | --- |
| siloxane 11 | 61.60 g:52.08 g | (1:1) |
| siloxane 12 | 36.96 g:72.92 g | (1:2.3) |

(1-5) Preparation of polyorganosiloxanes partly having alkylthiol groups by hydrolysis of a silane compound (Preparation process 5)

3-mercaptopropyltrimethoxysilane $(HS(CH_2)_3Si(OMe)_3)$ and tetraethoxysilane $(Si(OEt)_4)$ were mixed at the prescribed mixing ratios shown in Table 5 and then 62.5 ml of ethanol was added. The mixture was poured to a 1 liter three necked flask equipped with a stirrer and a condenser and stirred for an hour at 60° C. Next, 16.7 ml of 0.01 normal hydrochloric acid solution was added to the mixture solution and stirring was continued for 6 hours at 60° C. Then a mixture of 15 ml of hexane and 22.5 ml of ethanol was added while stirring at 60° C. and to the solution, was gradually dropped a solution in which 25.0 ml of 28% aqueous ammonia had been dissolved into 135.0 ml of pure water. After completion of dropping, stirring was continued for 4 hours at the same temperature to finish gelation.

After solvents and water were removed from the gelled mixture obtained under reduced pressure to dry, the dried gel was thoroughly washed with water and then dried again for 6 hours at 120° C. to obtain polyorganosiloxane.

Polyorganosiloxanes obtained by the preparation process 5 mentioned above are shown in Table 5.

TABLE 5

| Polyorganosiloxanes | $HS(CH_2)_3Si(OMe)_3$: $Si(OEt)_4$ weight | (mole ratio) |
| --- | --- | --- |
| siloxane 13 | 49.09 g:52.08 g | (1:1) |
| siloxane 14 | 29.45 g:72.92 g | (1:2.3) |

(2) Synthesis of polyorganosiloxane by silylating onto silica gel (2-1) Synthesis of polyorganosiloxane partly having halogenated alkyl groups by silylating onto silica gel (Preparation process 6)

After 10 g of commercial silica gel (MS Gel: produced by Dokai Kagaku Kogyo) was dried under reduced pressure for 4 hours at 100° C., it was placed in a 100 ml eggplant type flask. 25.0 g of 3-chloropropyltrimethoxysilane $((ClPr)Si(OMe)_3)$ was added therein, and then the mixture was heated with stirring for 4 hours at 100° C. After allowing the mixture to cool, it was filtered, and its white solid residue was thoroughly washed with methanol and then dried at 120° C. to obtain polyorganosiloxane 15.

(2-2) Synthesis of polyorganosiloxane partly having phenyl groups by silylating onto silica gel (Preparation process 7)

After 10 g of commercial silica gel (MS Gel: produced by Dokai Kagaku Kogyo) was dried under reduced pressure for 4 hours at 100° C., it was placed in a 100 ml eggplant type flask. 25.0 g of phenyltriethoxysilane $((Ph)Si(OEt)_3)$ was added therein, and then the mixture was heated with stirring for 4 hours at 100° C. After allowing the mixture to cool, it was filtered, and its white solid residue was thoroughly washed with methanol and then dried at 120° C. to obtain polyorganosiloxane 16.

(2-3) Synthesis of polyorganosiloxane partly having vinyl groups by silylating onto silica gel (Preparation process 8)

After 10 g of commercial silica gel (MS Gel: produced by Dokai Kagaku Kogyo) was dried under reduced pressure for 4 hours at 100° C., it was placed in a 100 ml eggplant type flask. 25.0 g of vinyltriethoxysilane $(CH_2=CHSi(OEt)_3)$ was added therein and then the mixture was heated with stirring for 4 hours at 100° C. After allowing the mixture to cool, it was filtered, and its white solid residue was thoroughly washed with methanol and then dried at 120° C. to obtain polyorganosiloxane 17.

(2-4) Synthesis of polyorganosiloxane partly having epoxy groups by silylating onto silica gel (Preparation process 9)

After 10 g of commercial silica gel (MS Gel: produced by Dokai Kagaku Kogyo) was dried under reduced pressure for 4 hours at 100° C., it was placed in a 100 ml eggplant type flask. 25.0 g of 2-(3,4-epoxycyclohexyl)ethyltrimethoxysilane $(C_6H_8OC_2H_2Si(OMe)_3)$ was added therein and then the mixture was heated with stirring for 4 hours at 100° C. After allowing the mixture to cool, it was filtered, and its white solid residue was thoroughly washed with methanol and then dried at 120° C. to obtain polyorganosiloxane 18.

(2-5) Synthesis of polyorganosiloxane partly having alkylthiol groups by silylating onto silica gel (Preparation process 10)

After 10 g of commercial silica gel (MS Gel: produced by Dokai Kagaku Kogyo) was dried under reduced pressure for 4 hours at 100° C., it was placed in a 100 ml eggplant type flask. 25.0 g of 3-mercaptopropyltrimethoxysilane $(HS(CH_2)_3Si(OMe)_3)$ was added therein and then the mixture was heated with stirring for 4 hours at 100° C. After allowing the mixture to cool, it was filtered, and its white solid residue was thoroughly washed with methanol and then dried at 120° C. to obtain polyorganosiloxane 19.

(3) Sulfonation of polyorganosiloxanes (3-1) Sulfonation of polyorganosiloxanes partly having halogenated alkyl groups (Sulfonation 1)

10.0 g of a polyorganosiloxane prepared by the aforementioned preparation process 1 or 6, 1.5 times as much anhydrous sodium sulfite as a halogenated alkyl group by mole and 100 ml of pure water were placed in a 300 ml flask, heated to reflux with stirring for 50 hours, cooled to room temperature, filtered, and the solid residue was separated. Then, the separated solid was thoroughly washed with pure water by filtration and dried under vacuum for 6 hours at 120° C. to obtain white solid. Furthermore, after the white solid obtained was mixed with 100 ml of 1N hydrochloric acid and stirred for 1 hour, the white solid was filtered and separated, washed thoroughly with pure water and dried for 6 hours at 120° C. This solid was used as a catalyst for hydration of olefins.

Polyorganosiloxane catalysts obtained by sulfonation process 1 mentioned above are shown in Table 6.

TABLE 6

| Polyorgano siloxane catalysts | Polyorgano siloxanes | Sulfonation processes | Acid exchange equivalents (mmol/g) |
| --- | --- | --- | --- |
| Catalyst 1 | Siloxane 1 | Sulfonation process 1 | 1.78 |
| Catalyst 2 | Siloxane 2 | Sulfonation process 1 | 1.20 |
| Catalyst 3 | Siloxane 3 | Sulfonation process 1 | 1.31 |
| Catalyst 4 | Siloxane 4 | Sulfonation process 1 | 0.41 |
| Catalyst 5 | Siloxane 15 | Sulfonation process 1 | 0.79 |

(3-2) Sulfonation of polyorganosiloxanes partly having phenyl groups (Sulfonation 2)

10.0 g of a polyorganosiloxane prepared by the aforementioned preparation process 2 or 7 and 100 ml of concentrated sulfuric acid were placed in a 300 ml flask, heated with stirring at 80° C. for 3 hours and cooled to room temperature. Then the mixture (slurry) was poured into a large amount of pure water and filtered to separate the solid. Furthermore, the solid separated was thoroughly washed with pure water and dried under reduced pressure at 120° C. for 6 hours to obtain the white solid. This solid was used as a catalyst for the hydration of olefins.

Polyorganosiloxane catalysts having sulfonic acid groups obtained by the aforementioned sulfonation process 2 are shown in Table 7.

TABLE 7

| Polyorgano siloxane catalysts | Polyorgano siloxanes | Sulfonation processes | Acid exchange equivalents (mmol/g) |
| --- | --- | --- | --- |
| Catalyst 6 | Siloxane 5 | Sulfonation process 2 | 0.91 |
| Catalyst 7 | Siloxane 6 | Sulfonation process 2 | 0.68 |
| Catalyst 8 | Siloxane 7 | Sulfonation process 2 | 0.79 |
| Catalyst 9 | Siloxane 8 | Sulfonation process 2 | 0.34 |
| Catalyst 10 | Siloxane 16 | Sulfonation process 2 | 0.57 |

(Sulfonation 3)

10.0 g of a polyorganosiloxane prepared by the aforementioned preparation process 2, 30 ml of chloroform and 20 ml of chlorosulfonic acid ($ClSO_3H$) dissolved in 30 ml of chloroform were placed in a 500 ml flask and heated with stirring at 80° C. for 3 hours to carry out sulfonation. After completion of the reaction, the mixture (slurry) was cooled to room temperature, poured into a large amount of ethanol and stirred thoroughly. Then pure water was added into this ethanol mixture and the mixture was filtered to separate the solid. Furthermore, the solid separated was thoroughly washed with pure water and dried under reduced pressure at 120° C. for 6 hours to obtain the white solid. This solid was used as a catalyst for the hydration of olefins.

Polyorganosiloxane catalysts obtained by the aforementioned sulfonation process 3 are shown in Table 8.

TABLE 8

| Polyorgano siloxane catalysts | Polyorgano siloxanes | Sulfonation processes | Acid exchange equivalents (mmol/g) |
| --- | --- | --- | --- |
| Catalyst 11 | Siloxane 5 | Sulfonation process 3 | 1.54 |
| Catalyst 12 | Siloxane 6 | Sulfonation process 3 | 1.12 |
| Catalyst 13 | Siloxane 7 | Sulfonation process 3 | 1.25 |
| Catalyst 14 | Siloxane 8 | Sulfonation process 3 | 0.46 |

(3-3) Sulfonation of polyorganosiloxanes partly having vinyl groups (Sulfonation 4)

15.0 g of a polyorganosiloxane prepared by the aforementioned preparation process 3 or 8, two times as much sodium hydrogen sulfite as a vinyl group by mole, four times as much anhydrous sodium sulfite as a vinyl group by equivalent and 500 ml of pure water were placed in a 1000 ml flask, heated to reflux with stirring while air was bubbled into the solution for 46 hours, cooled to room temperature and filtered to separate the solid. Moreover, the solid separated was thoroughly washed with pure water by filtration and dried at 120° C. for 6 hours to obtain the white solid. Furthermore, after this white solid was added to 200 ml of 1N hydrochloric acid and the solution was stirred for an hour, the solution was filtered to separate the solid. Then the solid was thoroughly washed with pure water and dried at 120° C. for 6 hours to obtain the white solid. This solid was used as a catalyst for the hydration of olefins.

Polyorganosiloxane catalysts obtained by the aforementioned sulfonation process 4 are shown in Table 9.

TABLE 9

| Polyorgano siloxane catalysts | Polyorgano siloxanes | Sulfonation processes | Acid exchange equivalents (mmol/g) |
| --- | --- | --- | --- |
| Catalyst 15 | Siloxane 9 | Sulfonation process 4 | 1.39 |
| Catalyst 16 | Siloxane 10 | Sulfonation process 4 | 1.44 |
| Catalyst 17 | Siloxane 17 | Sulfonation process 4 | 0.58 |

(3-4) Sulfonation of polyorganosiloxanes partly having epoxy groups (Sulfonation 5)

10.0 g of a polyorganosiloxane prepared by the aforementioned preparation process 4 or 9, two times as much sodium hydrogen sulfite as an epoxy group by mole, four times as much anhydrous sodium sulfite as an epoxy group by equivalent and 250 ml of pure water were placed in a 1000 ml flask, heated to reflux with stirring for 6 hours, cooled to room temperature and filtered to separate the solid. Moreover, the solid separated was thoroughly washed with pure water and dried at 120° C. for 6 hours to obtain the white solid. Furthermore, after this white solid was added to 200 ml of 1N hydrochloric acid and the solution was stirred for an hour, the solution was filtered to separate the solid. Then the solid was thoroughly washed with pure water and dried at 120° C. for 6 hours to obtain the white solid. This solid was used as a catalyst for the hydration of olefins.

Polyorganosiloxane catalysts obtained by the aforementioned sulfonation process 5 are shown in Table 10.

TABLE 10

| Polyorgano siloxane catalysts | Polyorgano siloxanes | Sulfonation processes | Acid exchange equivalents (mmol/g) |
|---|---|---|---|
| Catalyst 18 | Siloxane 11 | Sulfonation process 5 | 0.74 |
| Catalyst 19 | Siloxane 12 | Sulfonation process 5 | 1.12 |
| Catalyst 20 | Siloxane 18 | Sulfonation process 5 | 0.52 |

(3-5) Sulfonation of polyorganosiloxanes partly having alkylthiol groups (Sulfonation 6)

10 g of a polyorganosiloxane prepared by the aforementioned preparation process 5 or 10 was gradually added to 30 ml of concentrated nitric acid and the solution was stirred at room temperature for an hour. After completion of the reaction, the solid was separated by filtration, washed sufficiently with pure water and dried at 120° C. for 6 hours to obtain the white solid. This solid was used as a catalyst for the hydration of olefins.

Polyorganosiloxane catalysts obtained by the aforementioned sulfonation process 6 are shown in Table 11.

TABLE 11

| Polyorgano siloxane catalysts | Polyorgano siloxanes | Sulfonation processes | Acid exchange equivalents (mmol/g) |
|---|---|---|---|
| Catalyst 21 | Siloxane 13 | Sulfonation process 6 | 1.70 |
| Catalyst 22 | Siloxane 14 | Sulfonation process 6 | 1.78 |
| Catalyst 23 | Siloxane 19 | Sulfonation process 6 | 0.55 |

(4) Coating polyorganosiloxanes having sulfonic acid groups with silica 10 g of the aforementioned catalyst 2, 3, 7 or 8 and 25.0 ml of ethanol were placed in a 500 ml three necked flask equipped with a stirrer and a condenser, and the solution was stirred at 40° C. for an hour. Then 34.67 g (comparable to 10 g of $SiO_2$) of tetraethoxysilane ($Si(OEt)_4$) was added to the solution and the mixture was stirred for an hour at 40° C. Then 28.8 ml of pure water was gradually dropped to the mixture with stirring. After completion of dropping, stirring was continued at 80° C. for 20 hours to carry out silica coating. After coating, solvent and water were removed from the mixture under reduced pressure and the white solid obtained was dried at 120° C. to obtain a silica coated polyorganosiloxane catalyst having sulfonic acid groups.

Thus obtained catalysts are shown in Table 12.

TABLE 12

| Silica coated catalysts | Catalysts before coating | Acid exchange equivalents (mmol/g) |
|---|---|---|
| Catalyst 24 | Catalyst 2 | 0.68 |
| Catalyst 25 | Catalyst 3 | 0.75 |
| Catalyst 26 | Catalyst 7 | 0.40 |
| Catalyst 27 | Catalyst 8 | 0.42 |

(5) Silylation of polyorganosiloxanes having sulfonic acid groups 10 g of the aforementioned catalyst 2, 3, 7 or 8 was dried under reduced pressure at 100° C. for 4 hours and placed in a 100 ml eggplant type flask. Into the flask was added 25.0 g of triethylethoxysilane ($Et_3SiOEt$) and the mixture was stirred with heating at 100° C. for 4 hours. After allowing the mixture to cool, it was filtered, and the white solid residue thoroughly washed with methanol and dried at 120° C. to obtain a silylated polyorganosiloxane catalyst having sulfonic acid groups.

Thus obtained catalyst are shown in Table 13.

TABLE 13

| Silylated catalysts | Catalysts before silylation | Acid exchange equivalents (mmol/g) |
|---|---|---|
| Catalyst 28 | Catalyst 2 | 1.18 |
| Catalyst 29 | Catalyst 3 | 1.35 |
| Catalyst 30 | Catalyst 7 | 0.71 |
| Catalyst 31 | Catalyst 8 | 0.79 |

(6) Silylation of silica coated polyorganosiloxanes having sulfonic acid groups 10 g of the aforementioned catalyst 24, 25, 26 or 27 was dried under reduced pressure at 100° C. for 4 hours and placed in a 100 ml eggplant type flask. Into the flask was added 25.0 g of triethylethoxysilane ($Et_3SiOEt$) and the mixture was stirred with heating at 100° C. for 4 hours. After allowing the mixture to cool, it was filtered, and the white solid residue thoroughly washed with methanol and dried at 120° C. to obtain a silylated polyorganosiloxane catalyst having sulfonic acid groups.

Thus obtained catalysts are shown in Table 14.

TABLE 14

| Silylated catalysts | Catalysts before silylation | Acid exchange equivalents (mmol/g) |
|---|---|---|
| Catalyst 32 | Catalyst 24 | 0.58 |
| Catalyst 33 | Catalyst 25 | 0.59 |
| Catalyst 34 | Catalyst 26 | 0.31 |
| Catalyst 35 | Catalyst 27 | 0.32 |

Hydration Reactions

EXAMPLES 1 TO 23

After 3.0 g of a catalyst and 24.0 g (1.33 mol) of water were placed in a 70 ml autoclave, 12.0 g (0.285 mol) of propylene was injected with pressure into the autoclave and the mixture was stirred with heating at 140° C. for 5 hours to react. After completion of the reaction, the autoclave was cooled and the pressure was allowed to reduce. Then the reaction solution was analyzed by gas chromatography. As shown in Table 15, the results of analysis demonstrate that isopropyl alcohol was formed in good yields.

In all these examples, the formation of isopropyl ether by-product was not observed.

In addition, after completion of the reactions, the catalysts used were precipitated at the bottom of the reactor and the precipitates could be readily separated.

TABLE 15

| Example | Catalysts used | Yields of isopropyl alcohol (%) |
| --- | --- | --- |
| Example 1 | Catalyst 1 | 8.15 |
| Example 2 | Catalyst 2 | 4.86 |
| Example 3 | Catalyst 3 | 5.11 |
| Example 4 | Catalyst 4 | 2.12 |
| Example 5 | Catalyst 5 | 3.85 |
| Example 6 | Catalyst 6 | B.70 |
| Example 7 | Catalyst 7 | 5.51 |
| Example 8 | Catalyst 8 | 5.30 |
| Example 9 | Catalyst 9 | 3.40 |
| Example 10 | Catalyst 10 | 4.22 |
| Example 11 | Catalyst 11 | 17.40 |
| Example 12 | Catalyst 12 | 10.99 |
| Example 13 | Catalyst 13 | 12.80 |
| Example 14 | Catalyst 14 | 4.87 |
| Example 15 | Catalyst 15 | 6.76 |
| Example 16 | Catalyst 16 | 7.06 |
| Example 17 | Catalyst 17 | 2.52 |
| Example 18 | Catalyst 18 | 1.78 |
| Example 19 | Catalyst 19 | 5.28 |
| Example 20 | Catalyst 20 | 1.14 |
| Example 21 | Catalyst 21 | 8.01 |
| Example 22 | Catalyst 22 | 8.35 |
| Example 23 | Catalyst 23 | 2.64 |

Yields of isopropyl alcohol are based on charged propylene.

EXAMPLES 24 TO 27

After 6.0 g (comparable to 3.0 g of polyorganosiloxane having sulfonic acid groups) of the catalyst shown in Table 16 and 24.0 g (1.33 mol) of water were placed in a 70 ml autoclave, 12.0 g (0.285 mol) of propylene was injected with pressure into the autoclave and the mixture was stirred with heating at 140° C. for 5 hours to react. After completion of the reaction, the autoclave was cooled and the pressure was allowed to reduce. Then the reaction solution was analyzed by gas chromatography. As shown in Table 16, the results of analysis demonstrate that isopropyl alcohol was formed in better yields by using silica coated catalysts than those before silica coating.

In all these examples the formation of isopropyl ether by-product was not observed.

In addition, after completion of the reactions, the catalysts used were precipitated at the bottom of the reactor and the precipitates could be readily separated.

TABLE 16

| Example | Catalysts used | Yields of isopropyl alcohol (%) |
| --- | --- | --- |
| Example 24 | Catalyst 24 | 14.55 |
| Example 25 | Catalyst 25 | 15.02 |
| Example 26 | Catalyst 26 | 15.74 |
| Example 27 | Catalyst 27 | 15.56 |

Yields of isopropyl alcohol are based on charged propylene.

EXAMPLES 28 TO 31

After 3.0 g of the catalyst shown in Table 17 and 24.0 g (1.33 mol) of water were placed in a 70 ml autoclave, 12.0 g (0.285 mol) of propylene was injected with pressure into the autoclave and the mixture was stirred with heating at 140° C. for 5 hours to react. After completion of the reaction, the autoclave was cooled and the pressure was allowed to reduce. Then the reaction solution was analyzed by gas chromatography. As shown in Table 17, the results of analysis demonstrate that isopropyl alcohol was formed in better yields by using silylated catalysts than those before silylation.

In all these examples the formation of isopropyl ether by-product was not observed.

In addition, after completion of the reactions, the catalysts used were precipitated at the bottom of the reactor and the precipitates could be readily separated.

TABLE 17

| Example | Catalysts used | Yields of isopropyl alcohol (%) |
| --- | --- | --- |
| Example 28 | Catalyst 28 | 9.12 |
| Example 29 | Catalyst 29 | 9.96 |
| Example 30 | Catalyst 30 | 10.40 |
| Example 31 | Catalyst 31 | 10.65 |

Yields of isopropyl alcohol are based on charged propylene.

EXAMPLES 32 TO 35

After 6.0 g of the catalyst shown in Table 18 and 24.0 g (1.33 mol) of water were placed in a 70 ml autoclave, 12.0 g (0.285 mol) of propylene was injected with pressure into the autoclave and the mixture was stirred with heating at 140° C. for 5 hours to react. After completion of the reaction, the autoclave was cooled and the pressure was allowed to reduce. Then the reaction solution was analyzed by gas chromatography. As shown in Table 18, the results of analysis demonstrate that isopropyl alcohol was formed in better yields by using silylated catalysts than those before silylation. Also, silylation treatment after silica coating is found to be an effective means for improving catalyst activities.

In all these examples the formation of isopropyl ether by-product was not observed.

In addition, after completion of the reactions, the catalysts used were precipitated at the bottom of the reactor and the precipitates could be readily separated.

TABLE 18

| Example | Catalysts used | Yields of isopropyl alcohol (%) |
| --- | --- | --- |
| Example 32 | Catalyst 32 | 16.70 |
| Example 33 | Catalyst 33 | 17.46 |
| Example 34 | Catalyst 34 | 18.32 |
| Example 35 | Catalyst 35 | 18.67 |

Yields of isopropyl alcohol are based on charged propylene.

EXAMPLES 36 TO 41

Examples 3, 8, 25, 27, 33 and 35 were repeated under the same conditions except that the reaction temperature was 160° C. The results are shown in Table 19.

TABLE 19

| Example | Catalysts used | Yields (%) | iPA | DiPE |
|---|---|---|---|---|
| Example 36 | Catalyst 3 | | 12.73 | 0.10 |
| Example 37 | Catalyst 8 | | 17.68 | 0.15 |
| Example 38 | Catalyst 25 | | 33.98 | 0.31 |
| Example 39 | Catalyst 27 | | 38.41 | 0.35 |
| Example 40 | Catalyst 33 | | 36.98 | 0.44 |
| Example 41 | Catalyst 35 | | 39.51 | 0.58 | iPA=isopropyl alcohol; DiPE=diisopropyl ether

Yields of both compounds are represented by %, based on charged propylene.

EXAMPLES 42 TO 47

Examples 36 to 41 were repeated under the same conditions except that the amount of water as a raw material was 36.0 g. The results are shown in Table 20.

TABLE 20

| Example | Catalysts used | Yields (%) | iPA | DiPE |
|---|---|---|---|---|
| Example 42 | Catalyst 3 | | 12.73 | 0.10 |
| Example 43 | Catalyst 8 | | 17.68 | 0.11 |
| Example 44 | Catalyst 25 | | 44.98 | 0.23 |
| Example 45 | Catalyst 27 | | 48.51 | 0.27 |
| Example 46 | Catalyst 33 | | 52.98 | 0.25 |
| Example 47 | Catalyst 35 | | 60.36 | 0.32 | iPA=isopropyl alcohol; DiPE=diisopropyl ether

Yields of both compounds are represented by %, based on charged propylene.

EXAMPLES 48 TO 53

Examples 42 to 47 were repeated under the same conditions except that the amount of propylene as a raw material was 6.0 g, the reaction temperature was 200° C. and the reaction time was 0.5 hours. As a result, yields of isopropyl alcohol and diisopropyl ether were as those shown in Table 21.

TABLE 21

| Example | Catalysts used | Yields (%) | iPA | DiPE |
|---|---|---|---|---|
| Example 48 | Catalyst 3 | | 34.24 | 0.31 |
| Example 49 | Catalyst 8 | | 28.09 | 0.29 |
| Example 50 | Catalyst 25 | | 71.39 | 0.49 |
| Example 51 | Catalyst 27 | | 76.18 | 0.41 |
| Example 52 | Catalyst 33 | | 80.74 | 0.53 |
| Example 53 | Catalyst 35 | | 77.02 | 0.50 | iPA=isopropyl alcohol; DiPE=diisopropyl ether

Yields of both compounds are represented by %, based on charged propylene.

EXAMPLES 54 AND 55

Examples 48 and 49 were repeated under the same conditions. After completion of each reaction, only catalyst was left in the reactor and the reaction solution was separated and recovered to analyze. To the catalyst left in the reactor, the same amount of water and propylene as those used in each example were then added and each reaction was repeated under the same condition. This operation was repeated 5 times. As shown in Tables 22 and 23, the results demonstrate that repetition of each reaction does not decrease reactivity and the catalysts are stable at this temperature and under this condition.

TABLE 22

| Catalyst used | Repeated runs | Yields (%) | iPA | DiPE |
|---|---|---|---|---|
| Catalyst 3 | 1st Run | | 33.85 | 0.29 |
| | 2nd Run | | 34.10 | 0.30 |
| | 3rd Run | | 34.22 | 0.31 |
| | 4th Run | | 34.06 | 0.30 |
| | 5th Run | | 33.98 | 0.28 | iPA=isopropyl alcohol; DiPE=diisopropyl ether

Yields of both compounds are represented by %, based on charged propylene.

TABLE 23

| Catalyst used | Repeated runs | Yields (%) | iPA | DiPE |
|---|---|---|---|---|
| Catalyst 8 | 1st Run | | 28.15 | 0.29 |
| | 2nd Run | | 28.36 | 0.31 |
| | 3rd Run | | 27.12 | 0.28 |
| | 4th Run | | 29.00 | 0.31 |
| | 5th Run | | 28.74 | 0.29 | iPA=isopropyl alcohol; DiPE=diisopropyl ether

Yields of both compounds are represented by %, based on charged propylene.

EXAMPLES 56 AND 57

Examples 50 and 51 were repeated under the same conditions. After completion of each reaction, only catalyst was left in the reactor and the reaction solution was separated and recovered to analyze. To the catalyst left in the reactor, the same amount of water and propylene as those used in each example were then added and each reaction was repeated under the same condition. This operation was repeated 5 times. As shown in Tables 24 and 25, the results demonstrate that repetition of each reaction does not decrease reactivity and the catalysts are stable at this temperature and under this condition.

TABLE 24

| Catalyst used | Repeated runs | Yields (%) | iPA | DiPE |
|---|---|---|---|---|
| Catalyst 25 | 1st Run | | 71.68 | 0.49 |
| | 2nd Run | | 73.02 | 0.52 |
| | 3rd Run | | 72.22 | 0.50 |
| | 4th Run | | 71.69 | 0.50 |
| | 5th Run | | 71.25 | 0.49 | iPA=isopropyl alcohol; DiPE=diisopropyl ether

Yields of both compounds are represented by %, based on charged propylene.

TABLE 25

| Catalyst used | Repeated runs | Yields (%) | iPA | DiPE |
|---|---|---|---|---|
| Catalyst 27 | 1st Run | | 76.78 | 0.41 |
| | 2nd Run | | 76.90 | 0.40 |
| | 3rd Run | | 75.64 | 0.39 |
| | 4th Run | | 76.77 | 0.39 |
| | 5th Run | | 76.03 | 0.40 | iPA=isopropyl alcohol; DiPE=diisopropyl ether

Yields of both compounds are represented by %, based on charged propylene.

EXAMPLES 58 AND 59

Examples 52 and 53 were repeated under the same conditions. After completion of each reaction, only catalyst was left in the reactor and the reaction solution was separated and recovered to analyze. To the catalyst left in the reactor, the same amount of water and propylene as those used in each example were then added and each reaction was repeated under the same condition. This operation was repeated 5 times. As shown in Tables 25 and 26, the results demonstrate that repetition of each reaction does not decrease reactivity and the catalysts are stable at this temperature and under this condition.

TABLE 26

| Catalyst used | Repeated runs | Yields (%) | iPA | DiPE |
|---|---|---|---|---|
| Catalyst 33 | 1st Run | | 81.23 | 0.52 |
| | 2nd Run | | 81.39 | 0.54 |
| | 3rd Run | | 80.01 | 0.54 |
| | 4th Run | | 83.65 | 0.55 |
| | 5th Run | | 80.47 | 0.51 | iPA=isopropyl alcohol; DiPE=diisopropyl ether

Yields of both compounds are represented by %, based on charged propylene.

TABLE 27

| Catalyst used | Repeated runs | Yields (%) | iPA | DiPE |
|---|---|---|---|---|
| Catalyst 35 | 1st Run | | 76.92 | 0.50 |
| | 2nd Run | | 74.25 | 0.45 |
| | 3rd Run | | 73.59 | 0.50 |
| | 4th Run | | 75.64 | 0.51 |
| | 5th Run | | 76.39 | 0.49 | iPA=isopropyl alcohol; DiPE=diisopropyl ether

Yields of both compounds are represented by %, based on charged propylene.

COMPARATIVE EXAMPLE 1

Example 48 was repeated under the same conditions except that 3.0 g of Amberlite 15, cation-exchange resin, was used as the catalyst. The results obtained after the reaction was repeated 5 times show that the yield of isopropyl alcohol was slight and below the detection limit of analysis.

The catalyst was found to be apparently deteriorated by repeating the reaction under these conditions.

EXAMPLES 60 TO 71

Examples 3, 8, 25, 27, 33 and 35 were repeated under the same conditions except that 0.285 mol of ethylene or 1-butene was used instead of propylene. As shown in Table 28, the use of each olefin gives alcohols in good yields. Yields in Table 28 are all based on charged olefins.

In addition, alcohols produced are ethanol from ethylene and 2-butanol from 1-butene.

TABLE 28

| Example | Catalyst used | Olefins | Yields of alcohols (%) |
|---|---|---|---|
| Example 60 | Catalyst 3 | Ethylene | 4.95 |
| Example 61 | Catalyst 3 | 1-Butene | 6.88 |
| Example 62 | Catalyst 8 | Ethylene | 5.01 |
| Example 63 | Catalyst 8 | 1-Butene | 7.41 |
| Example 64 | Catalyst 25 | Ethylene | 11.69 |
| Example 65 | Catalyst 25 | 1-Butene | 15.98 |
| Example 66 | Catalyst 27 | Ethylene | 12.03 |
| Example 67 | Catalyst 27 | 1-Butene | 16.14 |
| Example 68 | Catalyst 33 | Ethylene | 12.05 |
| Example 69 | Catalyst 33 | 1-Butene | 16.01 |
| Example 70 | Catalyst 35 | Ethylene | 13.98 |
| Example 71 | Catalyst 35 | 1-Butene | 17.85 |

What is claimed is:

1. A process for producing alcohols comprising reacting olefins with water in the presence of a polyorganosiloxane having sulfonic acid groups and coated and/or silylated with at least one silane compound represented by the formula:

$$(R)_n Si(X)_{4-n}$$

wherein R represents at least one hydrocarbon group selected from the group consisting of aliphatic hydrocarbons having from 1 to 4 carbon atoms and aromatic hydrocarbons having from 6 to 15 carbon atoms; X represents an alkoxyl group, a chlorine atom, a bromine atom or an iodine atom; Si represents a silicon atom; and n represents an integer of from 0 to 3.

2. The process of claim 1, wherein said polyorganosiloxane having sulfonic acid groups is a polyorganosiloxane having aromatic sulfonic acid groups.

3. The process of claim 1, wherein said polyorganosiloxane having sulfonic acid groups is a polyorganosiloxane having alkyl sulfonic acid groups.

4. The process of claim 1, wherein said reaction of olefins with water is carried out under conditions where water exists in liquid state.

5. The process of claim 2, wherein said reaction of olefins with water is carried out under conditions where water exists in liquid state.

6. The process of claim 3, wherein said reaction of olefins with water is carried out under conditions where water exists in liquid state.

7. The process of claim 1, wherein said olefin is a lower olefin having from 2 to 6 carbon atoms.

8. The process of claim 2, wherein said olefin is a lower olefin having from 2 to 6 carbon atoms.

9. The process of claim 3, wherein said olefin is a lower olefin having from 2 to 6 carbon atoms.

10. The process of claim 4, wherein said olefin is a lower olefin having from 2 to 6 carbon atoms.

11. The process of claim 5, wherein said olefin is a lower olefin having from 2 to 6 carbon atoms.

12. The process of claim 6, wherein said olefin is a lower olefin having from 2 to 6 carbon atoms.

13. The process of claim 7, wherein said olefin is ethylene or propylene.

14. The process of claim 8, wherein said olefin is ethylene or propylene.

15. The process of claim 9, wherein said olefin is ethylene or propylene.

16. The process of claim 10, wherein said olefin is ethylene or propylene.

17. The process of claim 11, wherein said olefin is ethylene or propylene.

18. The process of claim 12, wherein said olefin is ethylene or propylene.

* * * * *